United States Patent [19]

Muysson

[11] Patent Number: 5,164,178
[45] Date of Patent: Nov. 17, 1992

[54] GRANULAR SOLID DEODORANT AND CORRESPONDING PACKAGE

[75] Inventor: Hans R. Muysson, Maarn, Netherlands

[73] Assignee: Beta Pictoris Inc., Milan, Italy

[21] Appl. No.: 207,371

[22] Filed: Jun. 15, 1988

[30] Foreign Application Priority Data

Nov. 24, 1987 [EP] European Pat. Off. ........ 87117294.6

[51] Int. Cl.$^5$ .................................................. A61K 7/46
[52] U.S. Cl. .................................. 424/76.4; 424/76.5; 206/5; 206/484; 206/823; 239/53; 239/60; 512/4; 428/35.3; 428/40; 428/42; 428/138; 428/321.1
[58] Field of Search ............. 424/76, 76.5, 76.4; 206/5, 632, 633, 484, 7; 239/53, 60; 428/35.3, 40, 42, 138, 321.1; 512/4

[56] References Cited

U.S. PATENT DOCUMENTS

| | | | |
|---|---|---|---|
| Re. 32,513 | 10/1987 | Seaber et al. | 239/60 |
| 3,031,146 | 12/1960 | Albamonte | 239/60 |
| 3,516,537 | 6/1966 | Dreyfus et al. | 206/632 |
| 3,797,742 | 3/1974 | Clark et al. | 239/60 |
| 3,953,378 | 4/1976 | Lassar | 512/4 |
| 3,961,043 | 6/1976 | Havar | 424/76.5 |
| 4,020,156 | 4/1977 | Murray et al. | 424/76.6 |
| 4,055,672 | 10/1977 | Hirsch et al. | 206/484 |
| 4,128,508 | 12/1978 | Munden | 424/76.4 |
| 4,254,910 | 3/1981 | Martin | 239/60 |
| 4,285,905 | 8/1981 | Feit | 424/76.4 |
| 4,297,233 | 10/1981 | Gualandi | 424/76.9 |
| 4,304,675 | 12/1981 | Corey et al. | 424/76.1 |
| 4,407,231 | 10/1983 | Colborn et al. | 264/4 |
| 4,580,581 | 4/1986 | Regle et al. | 239/60 |
| 4,605,165 | 8/1986 | Van Loveren et al. | 239/60 |
| 4,649,046 | 3/1987 | Kross | 424/76.4 |
| 4,720,417 | 1/1988 | Sweeny et al. | 428/321.5 |

OTHER PUBLICATIONS

Perry "Handbook for Chemical Engineers" Table 21-6 U.S. Sieve Series & Tyler Equivalents.

Primary Examiner—Henry F. Epstein
Assistant Examiner—Archene Turner
Attorney, Agent, or Firm—Michael J. Striker

[57] ABSTRACT

The solid granular deodorant consists of a porous granular $CaSO_4.2H_2O$ base, a portion of essential oils adsorbed on said porous granular base and microcapsules filled with another portion of the essential oils. The portion of the essential oils adsorbed on the granular base is present in an amount of from 2% to 18% by weight and the other portion of the essential oils in the microcapsules is present in an amount of from 0.5% to 4% by weight. The microcapsules are breakable by impacts, crushing or heating. This granular deodorant is packed in a sealed pouch which has micro-holes on one side covered by a removable, repositionable adhesive tape.

10 Claims, 1 Drawing Sheet

GRANULAR SOLID DEODORANT AND CORRESPONDING PACKAGE

BACKGROUND OF THE INVENTION

The present invention relates to a granular solid deodorant and a package for such deodorant which allows various utilizations.

Deodorants of the above kind are already known. They comprise a porous granular base, generally constitued by silica, alumina and other metallic oxides in lower percentages, on which essential oils of various fragrancies are absorbed.

The essential oil-impregnated granules are packaged in mono-dose pouches, which are emptied at the moment they are to be used, for instance in an ashtray.

Such granules, in contact with air, gradually release the absorbed perfume, with an intensity which is obviously higher in the initial phase, and decreases as the essential oils become exhausted.

This type of perfume release is not satisfactory because in some circumstances, it might be necessary to increase the impact of the released perfume. Moreover, it would be desirable, according to the circumstances, to be able to control the perfume release.

SUMMARY OF THE INVENTION

A purpose of the present invention is that of devising a granular solid deodorant which, besides the regular release of the perfume absorbed on the granules, is able under particular circumstances to give off an almost instantaneous release of perfume.

Another purpose of the invention is that of making the intensity of perfume release controllable according to its utilization.

According to the invention, the deodorant comprising a solid granular base impregnated with essential oils is characterized by the fact that essential oil-filled microcapsules are mixed to said granular base. The essential oil-filled microcapsules can advantageously be constituted by a thin layer of vegetable substances which may be broken as a consequence of impacts, crushing or heating, thus instantaneously releasing the perfume which they contain.

As a result, the instantaneous release of the microencapsulated perfume is added to the normal release of the perfume which is absorbed on the granules, with indisputable advantages for the user.

In fact, the release of the microencapsulated perfume is dependent on the actual utilization of the deodorant, and as a result its useful life can be markedly extended.

If, for instance, the deodorant is poured into an ashtray used in a home or an automobile, the microcapsules stay unbroken, but are gradually broken when a cigarette is put out, both because of crushing and heating due to the glowing end of the cigarette.

According to the invention, the granular base of the deodorant is constituted by $CaSO_4 \cdot 2H_2O$. The product color is neutral, apart from the various essential oils with different fragrances which are used.

In order to distinguish among the various fragrances, speckles made of plastic material, preferably polyester, and of different colors, are used by mixing them with the granular base and the microcapsules in an amount between 1% and 5% by weight, most preferably 2% by weight.

The concentration of the essential oils absorbed on the granular base and microencapsulated ranges respectively between 2% and 18%, and 0.5% and 4% by weight, most preferably 13% and 2% by weight, respectively.

The product as described above is packaged in individual sealed pouches, made of suitable materials, preferably polyester and polyethylene, having micro-holes on one side, covered by an adhesive tape, preferably made of metallized polyester, so that it is perfume-proof.

As a result, it is possible to use the deodorant either by tearing the pouch and pouring the content in any container, for instance an ashtray, or by leaving the granules in the pouch and removing the adhesive tape. The adhesive tape, rather than being completely removed, can be partially lifted to free only part of the underlying micro-holes on the pouch, so that the intensity of the perfume released can be regulated as desidered.

BRIEF DESCRIPTION OF THE DRAWING

The invention will now be illustrated in greater detail with reference to the attached drawing in which.

DESCRIPTION OF THE PREFERRED EMBODIMENT

Figure 1:
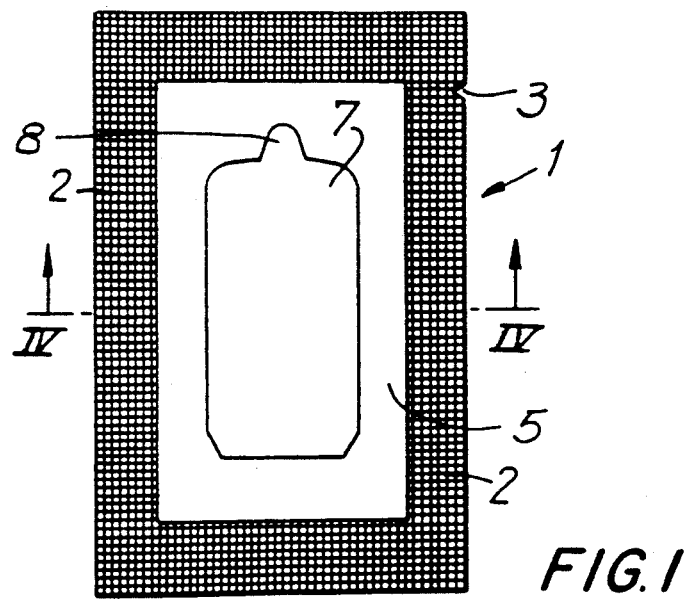
FIGS. 1, 2, and 3 are top views of a deodorant package according to the invention, having a side provided with the micro-holes and, respectively showing such side with an adhesive tape in position, partially lifted and completely removed.
Figure 4:
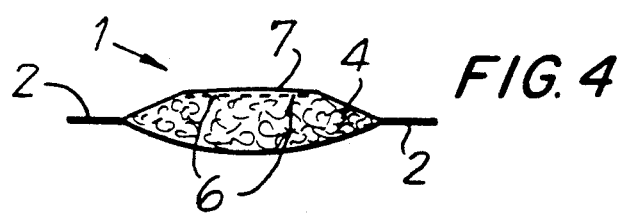
FIG. 4 is a view along the IV—IV line of FIG. 1.

With reference to the drawings, 1 indicates the pack of solid granular deodorant according to the invention, made of a rectangular pouch, with a seal 2 along its four edge portions.

The pouch 1 is preferably made of laminated polyester and polyethylene, and has a small indentation 3 on one edge portions to ease its being torn if it is desired to pour the granular deodorant 4 in a suitable container.

According to the invention, on one side 5 of the pouch 1 there are micro-holes 6 of a diameter such as to prevent the escape of the granular deodorant 4. The micro-holes 6 are covered by an adhesive tape 7, preferably made of metallized polyester in order to be perfume-proof.

The adhesive tape 7 has a non-adhesive finger tab 8 to provide an easier removal.

Figure 2:
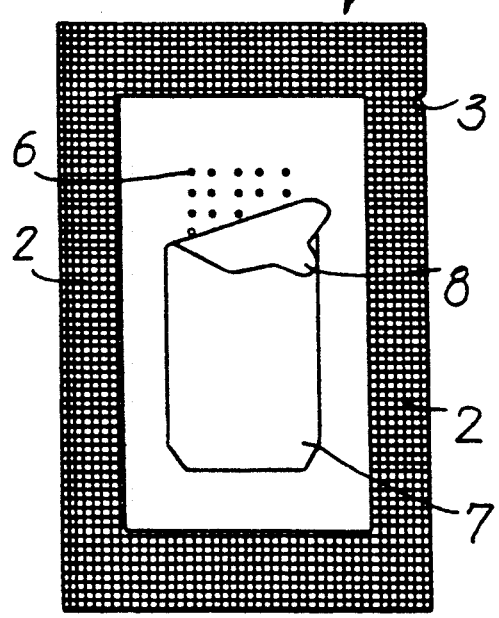
Figure 3:
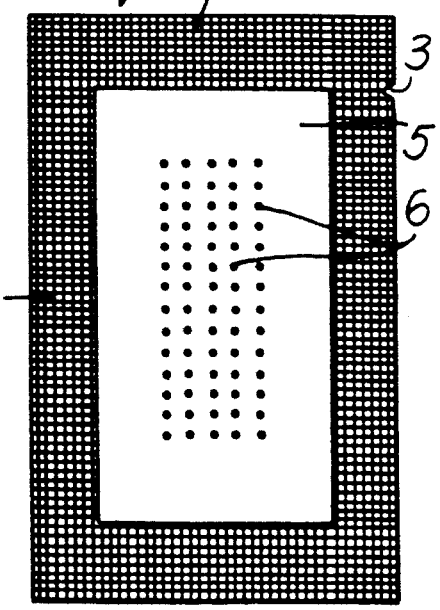

Under usage conditions, the adhesive tape 7 can be either partially lifted, as shown in FIG. 2, thus exposing only part of the micro-holes 6, or completely removed, as shown in FIG. 3, so that the intensity of the perfume release can be controlled within a wide range.

The tape 7, once lifted, does not lose its adhesiveness, so that it can be put back or lifted as many times as desired. The so structured pouch allows therefore very many utilizations of its content.

Deodorant 4 is constituted by a strongly adsorbent solid granular porous base, impregnated with essential oils, and by microcapsules, also containing essential oils with the same fragrance.

The granular base is conveniently made of $Ca\,SO_4 \cdot 2H_2O$, which is incombustible at the temperature of a lit cigarette, so that the product can also be used by pouring it in ashtrays.

Such granular base shows a neutral color apart from the essential oils.

The essential oil-filled microcapsules are made by a thin vegetable substances layer which is broken by impacts, crushing or heating.

The amount of essential oils absorbed by the granular base is equivalent to approximately 13% by weight of the total product, whereas the microencapsulated essential oils are about 2% by weight.

In order to differentiate the various product fragrances, polyester speckles of different corresponding colors are mixed with the product. An amount of speckles equivalent to approximately 2% by weight is sufficient for this purpose.

The product thus obtained provides a two-fold deodorant action: a regular action related to the perfume release from the granular base and an instantaneous action when the microcapsules are broken following impacts, crushing or heating.

A very advantageous utilization is thus obtained for the deodorant, whose useful life is longer than that of the conventional deodorants.

While the invention has been illustrated and described as embodied in a granular solid deodorant and corresponding package, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

I claim:

1. A solid granular deodorant consisting of a porous granular base consisting of $CaSO_4.2H_2O$ particles, a portion of essential oils adsorbed on said porous granular base and microcapsules filled with another portion of the essential oils, wherein the portion of said essential oils adsorbed on said granular base is present in an amount of from 2% to 18% by weight, the other portion of said essential oils in said microcapsules is present in an amount of from 0.5% to 4% by weight and said microcapsules are breakable by impacts, crushing or heating.

2. A solid granular deodorant as claimed in claim 1, wherein said portion of the essential oils adsorbed on said granular base is present in an amount of 13% by weight.

3. A solid granular deodorant as claimed in claim 1, wherein said other portion of the essential oils in said microcapsules is present in an amount of 2% by weight.

4. A solid granular deodorant as claimed in claim 1, wherein each of said microcapsules has a microcapsule wall made of a vegetable substance.

5. A solid granular deodorant, consisting essentially of a porous granular base having essential oils absorbed thereon, said porous granular base consisting essentially of $CaSO_4.2H_2O$ particles; a plurality of microcapsules filled with said essential oils mixed with said porous granular base and also from 1% to 5% by weight of a plurality of colored plastic speckles having a predetermined color, wherein said essential oils have a fragrance and said predetermined color of said speckles is chosen to indicate the fragrance of said essential oils, said microcapsules being breakable by impacts, crushing or heating.

6. A solid granular deodorant as claimed in claim 5, wherein said colored speckles are present in an amount of 2% by weight.

7. A package comprising a sealed pouch (1) having one side (5) provided with a plurality of micro-holes (6); a removable adhesive tape (7) applied to said one side (5) to cover said micro-holes (6) and a solid granular deodorant contained in said pouch (1), said solid granular deodorant consisting essentially of a plurality of porous $CaSO_4.2H_2O$ particles having essential oils absorbed thereon and a plurality of microcapsules filled with said essential oils mixed with said particles, said microcapsules being breakable by impacts, crushing or heating and said micro-holes being of a size such that said $CaSO_4.2H_2O$ particles do not escape from said pouch (1).

8. A package as claimed in claim 7, wherein said sealed pouch (1) is made of laminated polyester and polyethylene and said adhesive tape (7) is made of metallized polyester.

9. A package as claimed in claim 7, wherein said adhesive tape (7) is provided with a non-adhesive finger tab (8) and is repositionable after removal.

10. A package as claimed in claim 7, wherein said pouch (1) has a small indentation (3) in one edge portion thereof to facilitate opening.

* * * * *

UNITED STATES PATENT AND TRADEMARK OFFICE
CERTIFICATE OF CORRECTION

PATENT NO. : 5,164,178
DATED : November 17, 1992
INVENTOR(S) : Hans R. Muysson It is certified that error appears in the above-identified patent and that said Letters Patent is hereby corrected as shown below:

On the Title page, item [73], the Assignee's address should be --

Monrovia -Liberia--.

Signed and Sealed this

Ninth Day of November, 1993

Attest:

BRUCE LEHMAN

Attesting Officer

Commissioner of Patents and Trademarks